United States Patent [19]

Diaz et al.

[11] Patent Number: 5,569,775
[45] Date of Patent: Oct. 29, 1996

[54] PROCESS FOR SEPARATION OF DIMETHYLDICHLOROSILANE FROM METHYLTRICHLOROSILANE

[75] Inventors: Michael Diaz, Lexington, Ky.; Roland L. Halm; Michael A. McIntyre, both of Midland, Mich.; Oliver K. Wilding, Lagrange, Ky.

[73] Assignee: Dow Corning Corporation, Midland, Mich.

[21] Appl. No.: 564,529

[22] Filed: Nov. 29, 1995

[51] Int. Cl.$^6$ .................................................. C07F 7/08
[52] U.S. Cl. ............................................ 556/466; 210/690
[58] Field of Search ............................... 210/690; 556/466

[56] References Cited

U.S. PATENT DOCUMENTS

| | | | |
|---|---|---|---|
| 3,168,542 | 2/1965 | Shaffer | 556/466 |
| 3,441,584 | 4/1969 | Bazouin et al. | 556/466 |
| 3,646,092 | 2/1972 | Dathe | 556/466 |
| 4,402,796 | 9/1983 | Marko et al. | 556/466 X |
| 4,411,740 | 10/1983 | Flannigam et al. | 556/466 X |
| 5,290,342 | 3/1994 | Wikman et al. | 95/143 |
| 5,445,742 | 8/1995 | Bothe Almquist et al. | 210/670 |

*Primary Examiner*—Paul F. Shaver
*Attorney, Agent, or Firm*—William F. Boley

[57] ABSTRACT

A process for separating dimethyldichlorosilane from methyltrichlorosilane in a mixture. The process comprises contacting a mixture comprising methyltrichlorosilane and dimethyldichlorosilane with silica gel, where the dimethyldichlorosilane is selectively retained by the silica gel. The process provides for the recovery of a methyltrichlorosilane fraction reduced in dimethyldichlorosilane concentration. The present process is especially useful for removing low levels of dimethyldichlorosilane present as a contaminate in methyltrichlorosilane.

10 Claims, No Drawings

PROCESS FOR SEPARATION OF DIMETHYLDICHLOROSILANE FROM METHYLTRICHLOROSILANE

BACKGROUND OF INVENTION

The present invention is a process for separating dimethyldichlorosilane from methyltrichlorosilane in a mixture. The process comprises contacting a mixture comprising methyltrichlorosilane and dimethyldichlorosilane with silica gel, where the dimethyldichlorosilane is selectively retained by the silica gel. The process provides for the recovery of a methyltrichlorosilane fraction reduced in dimethyldichlorosilane concentration. The present process is especially useful for removing low levels of dimethyldichlorosilane from methyltrichlorosilane.

The commercial production of methylchlorosilanes involves the contact of methyl chloride with silicon metalloid in the presence of a catalyst comprising copper at temperatures within a range of about 300° C. to 350° C. Typically this process is optimized for the production of dimethyldichlorosilane, with lessor amounts of methylsilanes, methylchlorosilanes, methylhydrosilanes, $C_2$ to $C_7$ hydrocarbons, polysilanes, polysiloxanes, silylmethylenes, and other species being formed. This product mixture usually undergoes a series of process steps such as distillation, condensation, and the like to effect separation and recovery of commercially important individual components of the product mixture. However, standard separation techniques based on the difference in the boiling point between compounds become difficult and expensive when the compounds have similar boiling points. This situation exist with the separation of methyltrichlorosilane (b.p. 66.1° C.) and dimethyldichlorosilane (b.p. 70.1° C.). The present inventors have found that silica gel can selectively remove dimethyldichlorosilane when in mixture with methyttrichlorosilane and therefore provide an alternative method for separation of these two methylchlorosilanes. The present process is particularly effective for removing trace amounts of dimethyldichlorosilane from methyltrichlorosilane, thereby providing methyltrichlorosilane essentially free of dimethyldichlorosilane contamination.

Wilkman et al., U.S. Pat. No. 5,290,342, describe a process for separating ethylsilane from silane by selective adsorption of the ethylsilane onto activated carbon.

Bothe et al., U.S. Pat. No. 5,445,742, describe a process for purification of halosilanes. The process consists of contacting a mixture comprising a halosilane and a hydrocarbon with an adsorbent selective for the hydrocarbon. Examples of useful adsorbents taught by Bothe et al. include activated carbon, carbon molecular sieves, and high silica zeolite.

The cited art does not recognize that silica gel can be used to selectively separate dimethyldichlorosilane from methyltrichlorosilane.

SUMMARY OF INVENTION

The present invention is a process for separating dimethyldichlorosilane from methyltrichlorosilane in a mixture. The process comprises contacting a mixture comprising methyltrichlorosilane and dimethyldichlorosilane with silica gel, where the dimethyldichlorosilane is selectively retained by the silica gel. The process provides for the recovery of a methyltrichlorosilane fraction reduced in dimethyldichlorosilane concentration. The present process is especially useful for removing low levels of dimethyldichlorosilane present as a contaminate in methyltrichlorosilane.

DESCRIPTION OF INVENTION

The present invention is a process for separating dimethyldichlorosilane from methyltrichlorosilane in a mixture. The process comprises (A) contacting a mixture comprising methyltrichlorosilane and dimethyldichlorosilane with silica gel, where the dimethyldichlorosilane is selectively retained by the silica gel and (B) recovering methyltrichlorosilane reduced in dimethyldichlorosilane concentration.

In a preferred process the methyltrichlorosilane is present as a major component of the mixture while the dimethyldichlorosilane is present as a minor component of the mixture. More preferred is when the dimethyldichlorosilane comprises less than about 10 weight percent of the mixture. The mixture may comprise as minor components other compounds including similar boiling hydrocarbons and methylchlorosilanes.

The mixture comprising the methyltrichlorosilane and dimethyldichlorosilane can be contacted with the silica gel by standard methods. The mixture may be contacted with the silica gel as a liquid or as a gas. Preferred is when the mixture is contacted with the silica gel as a liquid. The process can be run as a batch, semi-continuous, or continuous process.

The temperature at which the mixture comprising the dimethyldichlorosilane and methyltrichlorosilane is contacted with the silica gel is not critical and can generally be within a range of about 0° C. to less than 100° C. A preferred temperature is within a range of about 10° C. to 50° C.

The pressure at which the mixture comprising dimethyldichlorosilane and methyltrichlorosilane is contacted with the silica gel is not critical and can generally be within a range of about 0.1 atm. to 10 arm. Preferred is when the process is conduct at a pressure within a range of about 1 atm. to 5 atm.

The silica gel useful in the present process can be of the regular-density, intermediate-density, or low density types. Such silica gels are described, for example, in Kirk-Othmer, Encyclopedia of Chemical Technology, Vol. 20, Third Edition, p. 773–774, John Wiley & Sons, N.Y., 1982. It is preferred that the silica gel have a surface area of at least about 200 m$^2$/g. More preferred is when the silica gel is of the regular-density type and has a surface area greater than about 500 m$^2$/g. The silica gel may contain up to about 10 weight percent alumina ($Al_2O_3$). Since chlorosilanes readily hydrolyze on contact with water, it may be necessary to at least partially dry the silica gel prior to use. Drying of the silica gel can be effected by standards methods known in the art such as by heating under reduced pressure. An example of a useful method for drying the silica gel is described in the Examples herein.

The silica gel selectively retains dimethyldichlorosilane relative to methyltrichlorosilane in a mixture. This selectivity allows for recovery of methyltrichlorosilane reduced in dimethyldichlorosilane concentration. Recovery of the methyltrichlorosilane reduced in dimethyldichlorosilane can be effected by standard methods for separating gases or liquids from solids. In a preferred process using a packed-bed of silica gel, recovery of the methyltrichlorosilane can consist of collecting the effluent from the column in a suitable container for chlorosilanes. Where the process is run as a batch process, for example in a stirred-tank reactor, recovery of the methyltrichlorosilane may be effected by filtration or by settling to separate the methyltrichlorosilane from the silica gel.

The present process may further comprise recovery of the dimethyldichlorosilane by removal from the silica gel. Removal from the silica gel may be effected by standard means such as using elevated temperatures, reduced pressure, or a combination of both. Removal of the dimethyldichlorosilane from the silica gel may be effected by, for example, elevated temperature and the use of an acid such as hydrogen chloride.

The following examples are provided to illustrate the present invention. These examples are not intended to limit the scope of the claims herein.

EXAMPLES

A number of silica gels were evaluated for their ability to selective remove dimethyldichlorosilane from a mixture consisting of methyltrichlorosilane containing 12,700 ppm dimethyldichlorosilane. Each silica gel sample was placed in a 50 ml flask. The silica gel sample size ranged from 10 to 20 grams. The flask was heated at about 350° C. under vacuum at about 30 mm Hg for six to eight hours to dry the silica gel. The flask was cooled and purged with dry nitrogen. The chlorosilane mixture was then injected into the cooled flask through a Viton rubber septum. An additional seal was provided by a teflon stop-cock. The flask was shaken at room temperature for about 16 hours. A liquid sample was taken from the flask and analyzed by gas chromatography using a flame ionization detector (GC-FID). The result of this analysis is reported in Table 1 as the parts per million $Me_2SiCl_2$ remaining in the liquid mixture after contact with the silica gel. The silica gels tested were products of Englehard, Greenwich, Conn. The manufacturer's designation for each of the silica gels along with typical physical properties is provided in Table 1.

TABLE 1

Silica Gel Selectivity for Dimethyldichlorosilane Adsorption

| Name | Surface Area ($m^2$/g) | Pore Vol. (cc/g) | Ave. Pore Size (Angstrom) | Alumina (Wt. %) | $Me_2SiCl_2$ (ppm) |
|---|---|---|---|---|---|
| Sorbead WS | 650 | 0.40 | 25 | 3 | 2,100 |
| Sorbead H | 750 | 0.47 | 25 | 3 | 1,160 |
| Sorbead R | 750 | 0.35 | 20 | 3 | 5,000 |
| Sorbead W | 275 | 0.30 | — | 10 | 7,200 |
| Sorbead AF | 700 | 0.40 | 25 | 0.3 | 9,250 |

We claim:

1. A process for separation of dimethyldichlorosilane from methyltrichlorosilane, the process comprising:

(A) contacting a mixture comprising methyltrichlorosilane and dimethyldichlorosilane with silica gel, where the dimethyldichlorosilane is selectively removed by the silica gel and (B) recovering methyltrichlorosilane reduced in dimethyldichlorosilane concentration.

2. A process according to claim 1, where the methyltrichlorosilane is present as a major component of the mixture and the dimethyldichlorosilane is present as a minor component of the mixture.

3. A process according to claim 1, where the dimethyldichlorosilane comprises less than about 10 weight percent of the mixture.

4. A process according to claim 1, where the mixture is in the liquid phase when contacted with the silica gel.

5. A process according to claim 1, where the mixture is contacted with the silica gel at a temperature within a range of about 0° C. to less than 100° C.

6. A process according to claim 1, where the mixture is contacted with the silica gel at a temperature within a range of about 10° C. to 50° C.

7. A process according to claim 1, where the silica gel has a surface area of at least about 200 $m^2$/g.

8. A process according to claim 1, where the silica gel has a surface area greater than about 500 $m^2$/g.

9. A process according to claim 1, where the silica gel contains up to about 10 weight percent alumina.

10. A process according to claim 1, where the dimethyldichlorosilane comprises less than about 10 weight percent of the mixture, the silica gel has a surface area greater than about 500 $m^2$/g, and the mixture is contacted with the silica gel at a temperature within a range of about 10° C. to 50° C.

* * * * *